(12) United States Patent
Rapold et al.

(10) Patent No.: US 8,961,620 B2
(45) Date of Patent: *Feb. 24, 2015

(54) PROCESS FOR DYEING OR LIGHTENING KERATIN FIBRES IN TWO PARTS, USING AN OIL-RICH ALKALINE DIRECT EMULSION BASED ON A SOLID NONIONIC SURFACTANT WITH AN HLB RANGING FROM 1.5 TO 10

(75) Inventors: Philippe Rapold, Paris (FR); Gautier Deconinck, Saint Gratien (FR); Caroline Goget, Summit, NJ (US); Luc Nicolas-Morgantini, Rully (FR); Frédéric Simonet, Clichy (FR); Sophie Bouxirot, Us (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/978,774

(22) PCT Filed: Jan. 9, 2012

(86) PCT No.: PCT/EP2012/050253
§ 371 (c)(1),
(2), (4) Date: Nov. 27, 2013

(87) PCT Pub. No.: WO2012/095394
PCT Pub. Date: Jul. 19, 2012

(65) Prior Publication Data
US 2014/0068876 A1   Mar. 13, 2014

Related U.S. Application Data

(60) Provisional application No. 61/436,015, filed on Jan. 25, 2011.

(30) Foreign Application Priority Data

Jan. 10, 2011   (FR) ...................................... 11 50176

(51) Int. Cl.
| | |
|---|---|
| *A61Q 5/10* | (2006.01) |
| *A61K 8/06* | (2006.01) |
| *A61K 8/31* | (2006.01) |
| *A61K 8/39* | (2006.01) |
| *A61K 8/41* | (2006.01) |
| *A61K 8/60* | (2006.01) |
| *A61K 8/86* | (2006.01) |
| *A61Q 5/08* | (2006.01) |

(52) U.S. Cl.
CPC . *A61K 8/06* (2013.01); *A61K 8/062* (2013.01); *A61K 8/31* (2013.01); *A61K 8/39* (2013.01); *A61K 8/41* (2013.01); *A61K 8/604* (2013.01); *A61K 8/86* (2013.01); *A61Q 5/10* (2013.01); *A61Q 5/08* (2013.01); *A61K 2800/882* (2013.01)
USPC ............ 8/405; 8/501; 8/580; 8/111; 132/202; 132/208

(58) Field of Classification Search
USPC ............... 8/405, 501, 580, 111; 132/202, 208
See application file for complete search history.

(56) References Cited

U.S. PATENT DOCUMENTS

| | | | |
|---|---|---|---|
| 4,003,699 A | 1/1977 | Rose et al. | |
| 4,137,180 A | 1/1979 | Naik et al. | |

(Continued)

FOREIGN PATENT DOCUMENTS

| | | |
|---|---|---|
| DE | 23 59 399 | 6/1975 |
| DE | 38 43 892 A1 | 5/1990 |

(Continued)

OTHER PUBLICATIONS

International Search Report and Written Opinion for PCT/EP2012/050253.
Todd, Charles et al., "Volatile Silicone Fluids for Cosmetic Formulations," Cosmetics and Toiletries, vol. 97, Jan. 1976, pp. 27-32.
Dowing in Arch. Dermatol, vol. 123, 1987, pp. 1381-1384.
Porter, M.R., "Handbook of Surfactants," 1991, pp. 116-178.

*Primary Examiner* — Eisa Elhilo
(74) *Attorney, Agent, or Firm* — The Marbury Law Group, PLLC

(57) ABSTRACT

The present invention relates to a process for dyeing or lightening keratin fibers, comprising the step of extemporaneously mixing at the time of use two compositions (A) and (B) and of applying the said mixture to the said fibers; the said mixture comprising at least 25% by weight of fatty substances relative to the total weight of the composition obtained from the mixing of two compositions (A)+(B); with: —(A) representing a composition in direct emulsion form whose content of oil(s) ii) is at least 30% by weight relative to the weight of composition (A), and comprising: i) at least one nonionic surfactant that is solid at room temperature and at atmospheric pressure, with an HLB ranging from 1.5 to 10; ii) at least one basifying agent; Hi) optionally at least one additional surfactant other than the solid nonionic surfactants (i), iv) optionally at least one dye; and —(B) representing a composition comprising at least one chemical oxidizing agent. A subject of the present invention is also a multi-compartment device and a composition (A) in direct emulsion form and the ready-to-use composition resulting from the mixing of compositions (A) and (B). The process according to the invention makes it possible to dye keratin fibers in a powerful, intense and/or homogeneous manner while at the same time being easy to prepare and to apply, since the mixture in the form of an oil-rich emulsion does not run, but remains localized at the point of application. The process of the invention also makes it possible to lighten keratin fibers in a noteworthy manner.

18 Claims, No Drawings

(56) References Cited

U.S. PATENT DOCUMENTS

| | | | |
|---|---|---|---|
| RE30,199 E | 1/1980 | Rose et al. | |
| 4,874,554 A | 10/1989 | Lange et al. | |
| 5,061,289 A | 10/1991 | Clausen et al. | |
| 5,380,340 A | 1/1995 | Neunhoeffer et al. | |
| 5,449,510 A * | 9/1995 | Gregoire et al. | 424/60 |
| 5,534,267 A | 7/1996 | Neunhoeffer et al. | |
| 5,663,366 A | 9/1997 | Neunhoeffer et al. | |
| 5,766,576 A | 6/1998 | Löwe et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 2002/0050013 A1 | 5/2002 | Vidal et al. | |
| 2003/0019051 A9 | 1/2003 | Vidal et al. | |
| 2010/0166688 A1* | 7/2010 | Hercouet et al. | 424/62 |
| 2010/0303748 A1 | 12/2010 | Hercouet | |

FOREIGN PATENT DOCUMENTS

| | | |
|---|---|---|
| DE | 41 33 957 A1 | 4/1993 |
| DE | 195 43 988 A1 | 5/1997 |
| EP | 0 770 375 A1 | 5/1997 |
| EP | 1 495 749 A2 | 1/2005 |
| FR | 2 733 749 A1 | 11/1995 |
| FR | 2 801 308 A1 | 5/2001 |
| FR | 2 886 136 A1 | 12/2006 |
| FR | 2 944 966 A1 | 11/2010 |
| FR | 2 946 875 A1 | 12/2010 |
| GB | 1 026 978 | 4/1966 |
| GB | 1 153 196 | 5/1969 |
| GB | 2 139 112 A | 11/1984 |
| JP | 02-019576 | 1/1990 |
| JP | 05-163124 | 6/1993 |
| WO | 94/08969 A1 | 4/1994 |
| WO | 94/08970 A1 | 4/1994 |
| WO | 96/15765 A1 | 5/1996 |
| WO | 02/13868 A1 | 2/2002 |

* cited by examiner

PROCESS FOR DYEING OR LIGHTENING KERATIN FIBRES IN TWO PARTS, USING AN OIL-RICH ALKALINE DIRECT EMULSION BASED ON A SOLID NONIONIC SURFACTANT WITH AN HLB RANGING FROM 1.5 TO 10

CROSS-REFERENCE TO RELATED APPLICATIONS

This is a national stage application of PCT/EP2012/050253, filed internationally on Jan. 9, 2012, which claims priority to U.S. Provisional Application No. 61/436,015, filed on Jan. 25, 2011; as well as French Application No. 1150176, filed on Jan. 10, 2011, all of which are incorporated herein by reference in their entireties.

The present invention relates to a process for dyeing or lightening keratin fibres such as the hair, using a composition in the form of a direct emulsion comprising at least 30% of oil(s) ii) and which contains 0 at least one nonionic surfactant that is solid at room temperature, with an HLB of between 1.5 and 10, ii) at least one oil, iii) at least one or basifying agent, optionally iv) at least one additional surfactant, which is preferably nonionic, with an HLB of greater than 10, and optionally v) at least one dye an oxidizing composition, at least 25% of fatty substances. A subject of the present invention is also a multi-compartment device and a composition in the form of an oil-rich direct emulsion comprising ingredients i) to v) as defined previously.

Among the methods for dyeing human keratin fibres, such as the hair, mention may be made of oxidation dyeing or permanent dyeing. More particularly, this dyeing method uses one or more oxidation dyes, usually one or more oxidation bases optionally combined with one or more couplers.

In general, oxidation bases are chosen from ortho- or para-phenylenediamines, ortho- or para-aminophenols and heterocyclic compounds. These oxidation bases are colourless or weakly coloured compounds which, when combined with oxidizing products, can give access to coloured species.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a wide range of colours to be obtained.

It is also possible to add to these compositions direct dyes, which are coloured, and colouring molecules that have affinity for fibres. The direct dyes generally used are chosen from nitrobenzene, anthraquinone, nitropyridine, azo, methine, azomethine, xanthene, acridine, azine and triarylmethane direct dyes. The presence of such compounds enables the obtained coloration to be further enriched with tints or enables the chromaticity of the obtained coloration to be increased.

Oxidation dyeing processes thus consist in using with these dye compositions a composition comprising at least one oxidizing agent, generally hydrogen peroxide, under alkaline pH conditions in the vast majority of cases. The role of this oxidizing agent is to reveal the coloration, via an oxidative condensation reaction between the oxidation dyes.

One of the difficulties arises from the fact that lightening processes are performed under alkaline conditions and that the alkaline agent most commonly used is aqueous ammonia. Aqueous ammonia is particularly advantageous in this type of process. Specifically, it enables adjustment of the pH of the composition to an alkaline pH in order to allow activation of the oxidizing agent. This agent also brings about swelling of the keratin fibre, with opening of the scales, which promotes the penetration of the oxidizing agent and of the oxidation dyes into the fibre and thus increases the efficacy of the reaction.

This basifying agent is highly volatile, and this causes unpleasantness to the user on account of the strong and fairly unpleasant characteristic odour of ammonia that is given off during the procedure.

Moreover, the amount of ammonia given off requires the use of levels which are greater than those necessary, in order to compensate for this loss. This is not without consequence for the user, who not only remains inconvenienced by the odour but may also be confronted with greater risks of intolerance, such as, for example, irritation of the scalp (stinging sensations).

The option purely and simply of replacing all or some of the aqueous ammonia with one or more other conventional basifying agents does not result in compositions that are as effective as those based on aqueous ammonia, particularly for the reason that these basifying agents do not provide sufficient lightening of pigmented fibres in the presence of the oxidizing agent or sufficient coloration in terms of intensity, power, chromaticity or homogeneity of the colour.

One of the objects of the present invention is to propose processes for dyeing and lightening keratin materials, especially keratin fibres such as the hair, which do not have the drawbacks of those used with the existing compositions, these drawbacks being caused by the presence of large amounts of ammonia, while at the same time remaining at least as efficient as regards the dyeing and lightening and the uniformity of this lightening.

Oxidation dyeing must moreover satisfy a certain number of requirements. Thus, it must be free of toxicological drawbacks, it must enable shades to be obtained in the desired intensity and it must show good resistance to external attacking factors such as light, bad weather, washing, permanent waving, perspiration and rubbing.

The dyeing process must also be make it possible to cover grey hair and, finally, must be as unselective as possible, i.e. it must produce the smallest possible colour differences along the same keratin fibre, which generally comprises areas that are differently sensitized (i.e. damaged) from its end to its root.

The compositions used in the dyeing process must also have good mixing and application properties on keratin fibres, and especially good rheological properties so as not to run down the face, onto the scalp or beyond the areas that it is proposed to dye, when they are applied.

Compositions in emulsion form must also be stable especially in terms of "phase separation", i.e. not returning to two phases with the organic phase on one side and the aqueous phase on the other. Now, when a composition in direct emulsion form is oil-rich, i.e. comprising more than 30% by weight of oil relative to the total weight of the composition, instability of the emulsion often arises, in particular at high temperature.

As regards processes for lightening keratin fibres, use is made of aqueous compositions comprising at least one oxidizing agent, under alkaline pH conditions in the vast majority of cases. The role of this oxidizing agent is to degrade the melanin of the hair, which, depending on the nature of the oxidizing agent present, leads to more or less pronounced lightening of the fibres.

Many attempts have been made in the field of lightening hair dyeing in order to improve the dyeing properties, for example using adjuvants. However, the choice of these adjuvants is difficult insofar as they must improve the dyeing properties of dye compositions without harming the other properties of these compositions. In particular, these adjuvants must not harm the keratin fibre-lightening properties and the dye application properties.

Similar problems arise in the case of bleaching compositions, where the addition of particular adjuvants must not harm the lightening properties of the composition or the application properties of the composition, especially the rheological properties.

The aim of the present invention is to obtain novel processes for the dyeing and in particular for the oxidation dyeing or lightening of keratin fibres, which do not have the drawbacks of the prior art.

More particularly, the aim of the present invention is to obtain a process for the oxidation dyeing of keratin fibres, with improved dyeing properties, which can achieve the desired lightening and which are easy to prepare and to apply, and especially for which the mixture does not run but remains localized at the point of application. The term "improved dyeing properties" in particular means an improvement in the power/intensity and/or uniformity of the dyeing result.

Another aim of the invention is also to obtain a process for lightening human keratin fibres such as the hair, which can achieve the desired lightening, which is easy to prepare, to mix and to apply, and especially for which the mixture does not run but remains localized at the point of application, and which is odourless or has very little unpleasant odour.

Another aim of the invention is to obtain oil-rich direct emulsions that are stable especially with respect to temperature, even in the absence of a thickener.

These aims are achieved by the present invention, one subject of which is a process for dyeing or lightening keratin fibres, which consists in extemporaneously mixing at the time of use two compositions (A) and (B) and in applying the said mixture to the said fibres; the said mixture comprising at least 25% by weight of fatty substances relative to the total weight of the composition obtained from the mixing of two compositions (A)+(B); with:

(A) representing a composition in direct emulsion form whose oil content is at least 30% by weight relative to the weight of composition (A), and comprising:
  i) at least one nonionic surfactant with a calculated HLB ranging from 1.5 to 10, which is solid at room temperature and at atmospheric pressure;
  ii) at least one basifying agent;
  iii) optionally at least one additional surfactant other than the solid nonionic surfactants i), which is preferably nonionic with an HLB of greater than 10;
  iv) optionally at least one dye; and
(B) representing a composition comprising at least one chemical oxidizing agent.

The invention also relates to a process for dyeing or lightening human keratin fibres, which consists in using the above-mentioned composition.

A subject of the invention is also composition (A) in direct emulsion form as defined previously.

Another subject of the invention is a ready-to-use composition, which comprises at least 25% by weight of fatty substances and comprising ingredients 0 and ii), and optionally iii) and iv), as defined previously and at least one oxidizing agent.

A subject of the invention is, similarly, a device comprising at least two compartments containing, in a first compartment, composition (A) as defined previously and, in a second compartment, composition (B) as defined previously.

Other characteristics and advantages of the invention will emerge more clearly on reading the description and the examples that follow.

In the text hereinbelow, unless otherwise indicated, the limits of a range of values are included in that range.

The human keratin fibres treated via the process according to the invention are preferably the hair.

The expression "at least one" is equivalent to the expression "one or more".

The term "direct emulsion" means a microscopically heterogeneous and macroscopically homogeneous mixture of two mutually immiscible liquid substances of oil-in-water (O/W) type. The emulsion is composed of an oily phase dispersed in an aqueous phase.

For the purposes of the present invention, the term "emulsion" thus means true emulsions, which are to be distinguished from microemulsions, which are thermodynamically stable systems, unlike true emulsions. The size of the droplets of the dispersed phase of the emulsions of the invention is preferably between 10 nm and 100 µm and preferably between 200 nm and 50 µm. This is the mean diameter D(3.2), which may be measured especially using a laser granulometer.

The direct emulsion may be prepared via standard emulsion preparation processes that are well known to those skilled in the art.

The term "fatty substance" means an organic compound that is insoluble in water at ordinary temperature (25° C.) and at atmospheric pressure (760 mmHg) (solubility of less than 5%, preferably 1% and even more preferentially 0.1%). They have in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane. The fatty substances of the invention are neither polyoxyalkylenated nor polyglycerolated.

The term "oxidizing agent" or "chemical oxidizing agent" according to the invention means an oxidizing agent other than atmospheric oxygen.

I—The Dyeing or Lightening Process of the Invention

The dyeing or lightening process according to the invention thus consists in applying the mixture of the two compositions (A) and (B) prepared just before use, particularly between 1 second and 15 minutes and preferentially 5 minutes before use, and in applying to the wet or dry human keratin fibres.

Composition (A) in direct emulsion form has an oil content of at least 30% by weight and preferentially of at least 50% by weight relative to the total weight of composition (A), and comprises:
  i) at least one nonionic surfactant that is solid at room temperature and at atmospheric pressure, with an HLB ranging from 1.5 to 10;
  ii) at least one basifying agent;
  iii) optionally at least one additional surfactant other than the solid nonionic surfactants i), which is preferably nonionic with an HLB of greater than 10;
  iv) optionally at least one dye; and
composition (B) comprising at least one chemical oxidizing agent.

When the process according to the invention is solely a lightening process, it does not incorporate a direct dye or an oxidation dye precursor (bases and couplers) usually used for the dyeing of human keratin fibres, or alternatively, if it does use direct dyes, the total content of the said dyes does not exceed 0.001% by weight relative to the weight of the composition once the mixing of compositions (A) and (B) has been performed.

Specifically, at such a content, only the composition derived from the mixing of (A) and (B) would possibly be dyed, i.e. no dyeing effect would be observed on the keratin fibres.

Preferentially, composition (A) does not contain any oxidation bases, coupler or direct dye when the process of the invention is solely a process for lightening keratin fibres.

According to another particular embodiment of the invention, the process is a process for dyeing keratin fibres using the mixture of compositions (A) and (B) as defined previously.

When the process according to the invention is a dyeing process, it uses at least one dye and more particularly direct dyes or oxidation dye precursors as defined below. If it uses direct dyes, the total content of the said direct dyes exceeds 0.001% by weight relative to the weight of the composition once the mixing of compositions (A) and (B) has been performed.

Preferentially, composition (A) contains oxidation bases, couplers and/or direct dyes.

The composition obtained from the mixing of (A) and (B) according to the invention is then left in place for a time usually ranging from one minute to one hour and preferably from 5 minutes to 30 minutes.

The temperature during the process is conventionally between room temperature (between 15 and 25° C.) and 80° C. and preferably between room temperature and 60° C.

After the treatment, the human keratin fibres are optionally rinsed with water, optionally washed with a shampoo and then rinsed with water, before being dried or left to dry.

The Ingredients (i)—Solid Nonionic Surfactant with an HLB Ranging from 1.5 to 10:

Composition (A) of the process of the invention comprises at least one surfactant with an HLB ranging from 1.5 to 10, which is solid at room temperature and at atmospheric pressure (25° C.; 1 atmosphere=760 mmHg).

The term HLB is well known to those skilled in the art, and denotes the hydrophilic-lipophilic balance of a surfactant.

The HLB or hydrophilic-lipophilic balance of the surfactant(s) used according to the invention is the HLB according to Griffin, defined in the publication *J. Soc. Cosm. Chem.* 1954 (volume 5), pages 249-256 or the experimentally determined HLB is as described in the book by the authors F. Puisieux and M. Seiller, entitled "Galenica 5: Les systèmes dispersés—Tome I—Agents de surface et émulsions—Chapitre IV—Notions de HLB et de HLB critique, pages 153-194—paragraph 1.1.2. Détermination de HLB par voie expérimentale [Experimental determination of HLB], pages 164-180.

It is preferably the calculated HLB values that should be taken into account.

The calculated HLB is defined as being the following coefficient:

calculated HLB=20×molar mass of the hydrophilic part/total molar mass.

For an oxyethylenated fatty alcohol, the hydrophilic part corresponds to the oxyethylene units condensed onto the fatty alcohol and the calculated HLB then corresponds to the Griffin HLB defined in the publication *J. Soc. Cosm. Chem.* 1954 (volume 5), pages 249-256. For an ester or an amide, the hydrophilic part is naturally defined as being beyond the carbonyl group, starting from the fatty chain(s). Needless to say, this magnitude is additive, and for a mixture of molecules, the calculated HLB corresponds to the mass-weighted average of the calculated HLB values for each molecule.

According to one particular embodiment of the invention, the melting point of the nonionic surfactant(s) with a calculated HLB ranging from 1.5 to 10 is greater than 30° C. and more preferentially greater than 40° C.

Examples of oxyalkylenated nonionic surfactants (i) that may be mentioned include:

oxyalkylenated ($C_8$-$C_{24}$)alkylphenols;

saturated or unsaturated, linear or branched, oxyalkylenated $C_8$-$C_{30}$ alcohols, saturated or unsaturated, linear or branched, optionally oxyalkylenated $C_8$-$C_{30}$ amides;

esters of saturated or unsaturated, linear or branched $C_8$-$C_{30}$ acids and of polyethylene glycols;

optionally polyoxyethylenated esters of saturated or unsaturated, linear or branched $C_8$-$C_{30}$ acids and of sorbitol;

polyglycerolated esters of saturated or unsaturated, linear or branched $C_8$-$C_{30}$ acids;

saturated or unsaturated, oxyethylenated plant oils;

$C_8$-$C_{30}$ alkyl glucosides;

condensates of ethylene oxide and/or of propylene oxide, inter alia, alone or as mixtures;

oxyethylenated and/or oxypropylenated silicones.

The surfactants bear a number of moles of ethylene oxide and/or of propylene oxide preferably ranging from 1 to 100, better still from 2 to 10 and even better still from 2 to 6.

As examples of solid nonionic compounds that may be used in the present invention, mention may be made of the following compounds:

| INCI name | Commercial reference | Calculated HLB |
|---|---|---|
| Steareth-2 | Brij 72 (Uniqema) | 4.9* |
| Steareth-3 | Isoxal 5 (Vevy) | 6.6* |
| Steareth-4 | Nikkol BS-4 (Nikko) | 7.9* |
| Steareth-5 | Jeecol SA-5 (Jeen) | 9.0* |
| Steareth-6 | Emalex 606 (Nihon Emulsion) | 9.9* |
| Ceteth-2 | Brij 52 (Uniqema) | 5.3* |
| Ceteth-3 | Emalex 103 (Nihon Emulsion) | 7.1* |
| Ceteth-4 | Lipocol C-4 (Lipo) | 8.4* |
| Ceteth-5 | Volpo C5 (Croda) | 9.5* |
| Ceteareth-2 | Volpo CS2 (Croda) | 5.1* |
| Ceteareth-3 | Jeecol CS-3 (Jeen) | 6.8* |
| Ceteareth-4 | Lipocol SC-4 (Lipo) | 8.1* |
| Ceteareth-5 | Volpo CS5 (Croda) | 9.2* |
| Beheneth-5 | Nikkol BB-5 (Nikko) | 8.1* |
| Cocamide MEA | Comperlan 100 (Cognis) | 4.8 |
| Cocamide MIPA | Ninol M-10 (Stepan) | 5.6 |
| Cocamide DEA | Comperlan KD (Cognis) | 7.1 |
| Stearamide MEA | Monamid S (Uniqema) | 3.7 |
| Stearamide DEA | Lipamide S (Lipo) | 5.6 |
| Myristamide DEA | Jeemide MRCA (Jeen) | 6.6 |
| Myristamide MEA | Witcamide MM (Witco) | 4.4 |
| Polyglyceryl-2 distearate | Emalex DSG-2 (Ikeda) | 4.7 |
| Polyglyceryl-3 distearate | Cithrol 2623 (Croda) | 6.2 |
| Polyglyceryl-2 stearate | Nikkol DGMS (Nikko) | 7.6 |
| Polyglyceryl-3 stearate | Radiasurf 7248 (Atofina) | 9.4 |
| PEG-2 Stearate | Sedefos 75 (Gattefosse) | 5.6 |
| PEG-3 Stearate | Tegin D 1102 (Goldschmidt) | 7.2 |
| PEG-4 Stearate | Cithrol 2MS (Croda) | 8.4 |
| Sorbitan distearate | Sorbon S-66 (Toho) | 4.7 |
| Sorbitan palmitate | Span 40 (Uniqema) | 8.1 |
| Sorbitan stearate | Span 60 (Uniqema) | 7.6 |
| Sorbitan tristearate | Span 65 (Uniqema) | 3.3 |
| Myristyl glucoside | Montanov 14 (SEPPIC) | 9.5 |
| Cetearyl glucoside | Tego Care CG 90 (Degussa) | 8.6 |
| Arachidyl glucoside | Montanov 202 (SEPPIC) | 7.8 |

*corresponding to the calculated HLB according to the Griffin method

Preferably, the nonionic surfactant(s) with an HLB ranging from 1.5 to 10, which are solid at room temperature and at atmospheric pressure, are chosen from mono- or polyoxyalkylenated nonionic surfactants, the oxyalkylene units more particularly being oxyethylene or oxypropylene units, or a combination thereof.

Advantageously, the nonionic surfactants do not comprise any oxypropylene units.

In accordance with one preferred embodiment of the invention, the oxyalkylenated nonionic surfactants are selected from oxyethylenated $C_8$-$C_{30}$ alcohols comprising from 1 to 6 mol of ethylene oxide.

More preferably, the said surfactants are chosen from solid nonionic surfactants with an HLB ranging from 2.5 to 8.

According to the invention, emulsion (A) preferably contains from 0.1% to 30% by weight of one or more surfactants with an HLB ranging from 1.5 to 10, which are solid at room temperature and at atmospheric pressure, even more preferentially from 0.5% to 20% by weight and better still from 1% to 10% by weight relative to the total weight of emulsion (A).

Emulsion (A) may contain other surfactants with an HLB of greater than 10. In this case, the surfactant(s) are chosen from nonionic, cationic, anionic and amphoteric surfactants and preferably from nonionic and anionic surfactants.

However, according to one particular embodiment, emulsion (A) does not contain any nonionic surfactants other than that or those with an HLB of between 1.5 and 10, which are solid at room temperature and at atmospheric pressure.

Composition (B) may also contain one or more nonionic surfactants with an HLB ranging from 1.5 to 10, which are solid at room temperature and at atmospheric pressure, the content thereof possibly ranging from 0.1% to 30% by weight, preferably from 0.5% to 20% by weight and even more particularly from 1% to 10% by weight relative to the total weight of composition (B).

In the ready-to-use composition resulting from the mixing of compositions (A) and (B), the content of nonionic surfactants with an HLB ranging from 1.5 to 10, which are solid at room temperature and at atmospheric pressure, may range from 0.1% to 30% by weight, preferably from 0.5% to 20% by weight and even more particularly from 1% to 10% by weight relative to the total weight of the mixture of compositions (A) and (B).

(ii)—The Oils:

The composition of part (A) of the process of the invention comprises at least 30% by weight of oil(s). The emulsion (A) may contain one or more oils of different nature.

The term "oil" means a "fatty substance" that is liquid, i.e. that is capable of flowing under the action of its own weight at room temperature (25° C.) and at atmospheric pressure ($10^5$ Pa).

Preferably, the viscosity at a temperature of 25° C. and at a shear rate of 1 $s^{-1}$ of the oil is between $10^{-3}$ Pa·s and 2 Pa·s. It may be measured using a Thermo Haake RS600 rheometer with cone-plate geometry or an equivalent machine.

Preferentially, composition (A) comprises at least 30% by weight of oil(s) and preferably at least 50% by weight of oil(s) relative to the total weight of the composition.

In particular, the oils are chosen from $C_6$-$C_{16}$ lower alkanes; non-silicone oils of animal origin; glycerides of plant or synthetic origin; linear or branched hydrocarbons of mineral or synthetic origin, bearing more than 16 carbon atoms; fluoro oils; liquid fatty alcohols; liquid fatty esters; non-salified liquid fatty acids; silicone oils; or mixtures thereof.

The term "non-silicone oil" means an oil not containing any silicon atoms (Si) and the term "silicone oil" means an oil containing at least one silicon atom.

As regards the lower alkanes, these alkanes comprise from 6 to 16 carbon atoms and are linear or branched, optionally cyclic. Examples that may be mentioned include hexane, dodecane and isoparaffins such as isohexadecane and isodecane.

An example of a non-silicone oil of animal origin that may be mentioned is perhydrosqualene.

Glycerides of plant or synthetic origin that may be mentioned include liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

As regards the linear or branched hydrocarbons of mineral or synthetic origin, containing more than 16 carbon atoms, mention may be made most particularly of volatile or non-volatile liquid paraffins, and derivatives thereof, petroleum jelly, liquid petroleum jelly, polydecenes, and hydrogenated polyisobutene such as Parleam®.

The fluoro oils may be chosen especially from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The liquid fatty alcohols, thus different from the solid fatty alcohols (i), which are suitable for use in the invention are selected more particularly from unsaturated or branched alcohols comprising from 8 to 30 carbon atoms. Examples that may be mentioned include 2-octyldodecan-1-ol, 2-butyloctanol, 2-hexyldecanol, 2-undecylpentadecanol, oleyl alcohol and linoleyl alcohol.

The fatty acids that may be used in the context of the invention are more particularly chosen from unsaturated or branched carboxylic acids comprising from 6 to 30 carbon atoms and in particular from 9 to 30 carbon atoms. They are advantageously chosen from oleic acid, linoleic acid, linolenic acid and isostearic acid.

As regards the esters of a fatty acid and/or of a fatty alcohol, which are different from the solid esters (ii) and different from the glycerides mentioned above, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, propylene glycol dicaprylate, butyl stearate, isobutyl stearate; dioctyl malate, hexyl laurate, 2-hexyldecyl laurate, isononyl isononanoate or cetyl octanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include saccharose, glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, and polyesters, and mixtures thereof.

These esters may be chosen, for example, from oleates, laurates, palmitates, myristates, behenates, cocoates, stearates, linoleates, linolenates, caprates and arachidonates, or mixtures thereof, such as, in particular, oleopalmitate, oleostearate or palmitostearate mixed esters.

More particularly, use is made of monoesters and diesters and in particular of sucrose, glucose or methylglucose mono- or dioleates, stearates, behenates, oleopalmitates, linoleates, linolenates or oleostearates.

An example that may be mentioned is the product sold under the name Glucate® DO by the company Amerchol, which is a methylglucose dioleate.

Among the sugar esters, it is also possible to use pentaerythrityl esters, preferably pentaerythrityl tetraisostearate, pentaerythrityl tetraoctanoate, and caprylic and capric hexaesters as a mixture with dipentaerythritol.

The term "liquid silicone" means an organopolysiloxane that is liquid at ordinary temperature (25° C.) and at atmospheric pressure (760 mmHg; i.e. $1.013 \times 10^5$ Pa).

Preferably, the silicone is chosen from liquid polydialkylsiloxanes, especially liquid polydimethylsiloxanes (PDMS) and liquid polyorganosiloxanes comprising at least one aryl group.

These silicones may also be organomodified. The organomodified silicones that may be used in accordance with the invention are liquid silicones as defined previously, comprising in their structure one or more organofunctional groups attached via a hydrocarbon-based group.

Organopolysiloxanes are defined in greater detail in Walter Noll's "Chemistry and Technology of Silicones" (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide or Silbione® 70045 V5 by Rhodia, and dodecamethylcyclopentasiloxane sold under the name Silsoft 1217 by Momentive Performance Materials, and mixtures thereof.

Mention may also be made of cyclocopolymers of the dimethylsiloxane/methylalkylsiloxane type, such as Volatile Silicone® FZ 3109 sold by the company Union Carbide, of formula:

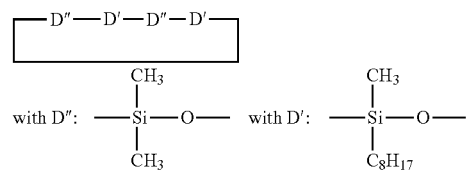

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)-neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers: Volatile Silicone Fluids for Cosmetics. The viscosity of the silicones is measured at 25° C. according to ASTM standard 445 Appendix C.

Non-volatile polydialkylsiloxanes may also be used.

These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm²/s;

the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups are polydiarylsiloxanes, especially polydiphenylsiloxanes and polyalkylarylsiloxanes. Examples that may be mentioned include the products sold under the following names:

the Silbione® oils of the 70 641 series from Rhodia;

the oils of the series Rhodorsil® 70 633 and 763 from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250 and SF 1265.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

According to one preferred variant, the oil(s) are chosen from $C_6$-$C_{16}$ lower alkanes; glycerides of plant or synthetic origin; linear or branched hydrocarbons of mineral or synthetic origin containing more than 16 carbon atoms; liquid fatty alcohols; liquid fatty esters; or mixtures thereof.

Even more preferentially, the oil(s) are chosen from $C_6$-$C_{16}$ lower alkanes; linear or branched hydrocarbons of mineral or synthetic origin containing more than 16 carbon atoms; liquid fatty alcohols; or mixtures thereof.

Preferably, the oil(s) are chosen from liquid petroleum jelly, polydecenes, octyldodecanol and isostearyl alcohol, or mixtures thereof.

In the ready-to-use composition resulting from the mixing of compositions (A) and (B), the amount of oil may represent from 7.5% to 60% of the total weight of the composition. Preferably, the ready-to-use composition resulting from the mixing of compositions (A) and (B) comprises at least 25% of oil(s).

Composition (B) may comprise at least one oil. If it contains oils, the total content thereof may range from 0.5% to 40% of the weight of composition (B).

(iii)—The Basifying Agents:

The process according to the invention also uses one or more basifying agents.

The basifying agent(s) may be mineral or organic or hybrid.

The mineral basifying agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chains comprising more than ten carbon atoms.

The organic basifying agent(s) are chosen, for example, from alkanolamines, oxyethylenated and/or oxypropylenated ethylenediamines, amino acids and the compounds of formula (I) below:

in which formula (I) W is a $C_1$-$C_6$ divalent alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl or $C_1$-$C_6$ hydroxyalkyl or $C_1$-$C_6$ aminoalkyl radical.

Examples of amines of formula (I) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (II) below:

in which formula (II) R represents a group chosen from:

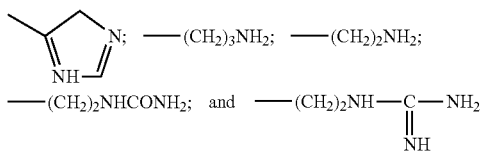 ——(CH$_2$)$_3$NH$_2$; ——(CH$_2$)$_2$NH$_2$;

——(CH$_2$)$_2$NHCONH$_2$; and ——(CH$_2$)$_2$NH—C—NH$_2$
$\qquad\qquad\qquad\qquad\qquad\qquad\qquad\quad\;\;\|$
$\qquad\qquad\qquad\qquad\qquad\qquad\qquad\quad$NH The compounds corresponding to formula (II) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and baleine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-[amino(imino)methyl]amino)ethane-1-sulfonic acid.

Preferably, the organic amine present in composition (A) of the invention is an alkanolamine. Even more preferentially, the basifying agent is monoethanolamine (MEA).

Hybrid compounds that may be mentioned include the salts of the amines mentioned previously with acids such as carbonic acid or hydrochloric acid.

Guanidine carbonate or monoethanolamine hydrochloride may be used in particular.

Advantageously, compositions (A) and (B) according to the invention and the ready-to-use composition have a content of basifying agent(s) ranging from 0.01% to 30% by weight and preferably from 0.1% to 20% by weight relative to the weight of the composition obtained from the mixing of (A) and (B).

Preferably, composition (B) does not contain any basifying agent.

According to one particular embodiment, the process according to the invention preferably does not use aqueous ammonia, or a salt thereof, as basifying agent. According to this particular embodiment, if, however, it were used in the process, its content would not exceed 0.03% by weight (expressed as NH$_3$) and preferably would not exceed 0.01% by weight relative to the weight of the composition obtained from the mixing of (A) and (B). Preferably, if composition (A) comprises aqueous ammonia, or a salt thereof, then the amount of basifying agent(s) is greater than that of the aqueous ammonia (expressed as NH$_3$).

(iii)—Additional Surfactants:

According to one particular embodiment, the process of the invention and the composition of the invention may comprise at least one additional surfactant other than the solid nonionic surfactants (i).

In particular, the additional surfactant(s) are chosen from nonionic surfactants or from anionic, amphoteric, cationic or nonionic surfactants, and preferentially nonionic surfactants.

The term "anionic surfactant" means a surfactant comprising, as ionic or ionizable groups, only anionic groups. These anionic groups are preferably chosen from the groups —C(O)OH, —C(O)O$^-$, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$, =POH, =PO$^-$, the anionic parts comprising a cationic counterion such as an alkali metal, an alkaline-earth metal or an ammonium.

Mention may be made, as examples of anionic surfactants that may be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids can be selected from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, the ammonium salts, the amine salts and in particular amino alcohol salts or the alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxyl-methyl)aminomethane salts.

Alkali metal or alkaline-earth metal salts and in particular the sodium or magnesium salts are preferably used.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, especially in the form of alkali metal, ammonium, amino alcohol and alkaline-earth metal salts, or a mixture of these compounds.

It is particularly preferred to use ($C_{12}$-$C_{20}$)alkyl sulfates, ($C_{12}$-$C_{20}$)alkyl ether sulfates comprising from 2 to 20 ethylene oxide units, especially in the form of alkali metal, ammonium, amino alcohol and alkaline-earth metal salts, or a mixture of these compounds. Better still, use is made of sodium lauryl ether sulfate containing 2.2 mol of ethylene oxide.

The amphoteric or zwitterionic surfactant(s), which are preferably nonsilicone, that may be used in the present invention may especially be derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of ($C_8$-$C_{20}$)alkylbetaines, sulfobetaines, ($C_8$-$C_{20}$)alkylamido($C_3$-$C_8$)alkylbetaines and ($C_8$-$C_{20}$)alkylamido($C_6$-$C_8$)alkylsulfobetaines.

Among the optionally quaternized secondary or tertiary aliphatic amine derivatives that can be used, as defined above, mention may also be made of the compounds of respective structures (III) and (IV) below:

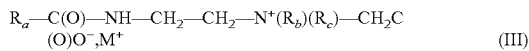

in which formula (III):
$R_a$ represents a $C_{10}$-$C_{30}$ alkyl or alkenyl group derived from an acid $R_aC(O)OH$ preferably present in hydrolysed coconut oil, or a heptyl, nonyl or undecyl group;
$R_b$ represents a beta-hydroxyethyl group; and
$R_c$ represents a carboxymethyl group;
$M^+$ represents a cationic counterion derived from an alkali metal or alkaline-earth metal, such as sodium, an ammonium ion or an ion derived from an organic amine, and

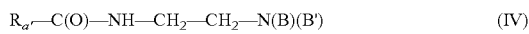

in which formula (IV):
B represents the group $—CH_2—CH_2—O—X'$;
B' represents the group $—(CH_2)_zY'$, with z=1 or 2;
X' represents the group $—CH_2—C(O)OH$, $—CH_2—C(O)OZ'$, $—CH_2—CH_2—C(O)OH$, $—CH_2—CH_2—C(O)OZ'$, or a hydrogen atom;
Y' represents the group $—C(O)OH$, $—C(O)OZ'$, $—CH_2—CH(OH)—SO_3H$ or the group $—CH_2—CH(OH)—SO_3—Z'$;
Z' represents a cationic counterion derived from an alkali metal or alkaline-earth metal, such as sodium, an ammonium ion or an ion derived from an organic amine;
$R_{a'}$ represents a $C_{10}$-$C_{30}$ alkyl or alkenyl group of an acid $R_a—C(O)OH$ preferably present in coconut oil or in hydrolysed linseed oil, an alkyl group, especially of $C_{17}$ and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caplyoamphodipropionate, lauroampho-dipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above, use is preferably made of $(C_8-C_{20})$alkylbetaines such as cocoylbetaine, and $(C_8-C_{20})$alkylamido$(C_3-C_8)$alkylbetaines such as cocamidopropylbetaine, and mixtures thereof. More preferentially, the amphoteric or zwitterionic surfactant(s) are chosen from cocamidopropylbetaine and cocoylbetaine.

The cationic surfactant(s) that can be used in the compositions of the present invention comprise, for example, salts of optionally polyoxyalkylenated primary, secondary or tertiary fatty amines, quaternary ammonium salts, and mixtures thereof.

Examples of quaternary ammonium salts that may especially be mentioned include:
those corresponding to the general formula (V) below:

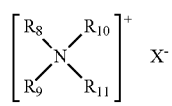

in which formula (V) the groups $R_8$ to $R_{11}$, which may be identical or different, represent a linear or branched aliphatic group comprising from 1 to 30 carbon atoms or an aromatic group such as aryl or alkylaryl, at least one of the groups $R_8$ to $R_{11}$ comprising from 8 to 30 carbon atoms and preferably from 12 to 24 carbon atoms. The aliphatic groups may comprise heteroatoms such as, in particular, oxygen, nitrogen, sulfur and halogens.

The aliphatic groups are chosen, for example, from $C_1$-$C_{30}$ alkyl, $C_1$-$C_{30}$ alkoxy, polyoxy$(C_2$-$C_6)$alkylene, $C_1$-$C_{30}$ alkylamide, $(C_{12}$-$C_{22})$alkylamido$(C_2$-$C_6)$alkyl, $(C_{12}$-$C_{22})$alkylacetate, $C_1$-$C_{30}$ hydroxyalkyl, $X^-$ is an anionic counterion chosen from halides, phosphates, acetates, lactates, $(C_1$-$C_4)$ alkyl sulfates, and $(C_1$-$C_4)$alkyl- or $(C_1$-$C_4)$alkylarylsulfonates.

Among the quaternary ammonium salts of formula (VII), preference is given firstly to tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (VI) below:

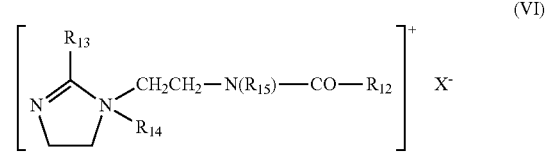

in which formula (VI) $R_{12}$ represents an alkyl or alkenyl group comprising from 8 to 30 carbon atoms, for example fatty acid derivatives of tallow, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ represents an anion counterion chosen from halides, phosphates, acetates, lactates, $(C_1$-$C_4)$alkyl sulfates and $(C_1$-$C_4)$alkyl- or $(C_1$-$C_4)$alkylaryl-sulfonates. $R_{12}$ and $R_{13}$ preferably denote a mixture of alkyl or alkenyl groups comprising from 12 to 21 carbon atoms, for example tallow fatty acid derivatives, $R_{14}$ denotes a methyl group, and $R_{15}$ denotes a hydrogen atom. Such a product is sold, for example, under the name Rewoquat® W 75 by the company Rewo;

quaternary diammonium or triammonium salts, particularly of formula (VII) below:

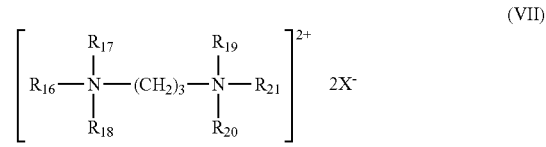

in which formula (VII) $R_{16}$ denotes an alkyl group comprising for about 16 to 30 carbon atoms, optionally hydroxylated and/or interrupted with one or more oxygen atoms; $R_{17}$ is chosen from hydrogen, an alkyl group comprising from 1 to 4 carbon atoms or a group —(CH$_2$)$_3$—N$^+$(R$_{16a}$)(R$_{17a}$)(R$_{18a}$); $R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms, and X$^-$ is an anion chosen from the group of halides, acetates, phosphates, nitrates, (C$_1$-C$_4$)alkyl sulfates and (C$_1$-C$_4$)alkyl- or (C$_1$-C$_4$) alkylaryl-sulfonates, in particular methyl sulfate and ethyl sulfate. Such compounds are, for example, Finquat CT-P, sold by the company Finetex (Quaternium 89), and Finquat CT, sold by the company Finetex (Quaternium 75);

quaternary ammonium salts comprising one or more ester functions, such as those of formula (VIII) below:

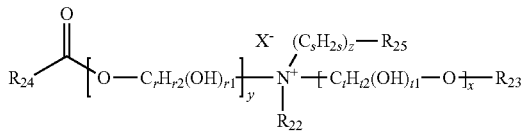

(VIII)

in which formula (VIII):

$R_{22}$ is chosen from C$_1$-C$_6$ alkyl and C$_1$-C$_6$ hydroxyalkyl or dihydroxyalkyl groups;

$R_{23}$ is chosen from:
the group

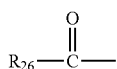

linear or branched, saturated or unsaturated C$_1$-C$_{22}$ hydrocarbon-based groups R$_{27}$,
a hydrogen atom;

$R_{25}$ is selected from:
the group

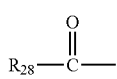

linear or branched, saturated or unsaturated C$_1$-C$_6$ hydrocarbon-based groups R$_{29}$,
a hydrogen atom;

$R_{24}$, $R_{26}$ and $R_{28}$, which may be identical or different, are chosen from linear or branched, saturated or unsaturated C$_7$-C$_{21}$ hydrocarbon-based groups;

r, s and t, which may be identical or different, are integers ranging from 2 to 6;

r1 and t1, which may be identical or different, are equal to 0 or 1, with r2+r1=2r and t1+t2=2t y is an integer ranging from 1 to 10;

x and z, which may be identical or different, are integers ranging from 0 to 10;

X$^-$ represents an organic or inorganic anionic counterion;

with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and may contain from 12 to 22 carbon atoms, or may be short and may contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated C$_{11}$-C$_{21}$ hydrocarbon-based groups, and more particularly from linear or branched, saturated or unsaturated C$_{11}$-C$_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion X$^-$ is preferably a halide, preferably such as chloride, bromide or iodide; a (C$_1$-C$_4$)alkyl sulfate or a (C$_1$-C$_4$)alkyl- or (C$^1$-C$_4$)alkylaryl-sulfonate. However, use may be made of methanesulfonate, phosphate, nitrate, tosylate, an anion derived from an organic acid, such as acetate or lactate, or any other anion compatible with the ammonium containing an ester function.

The anionic counterion X$^-$ is even more particularly chloride, methyl sulfate and or ethyl sulfate.

Use is made more particularly, in the composition according to the invention, of the ammonium salts of formula (VIII) in which:

$R_{22}$ denotes a methyl or ethyl group,
x and y are equal to 1,
z is equal to 0 or 1,
r, s and t are equal to 2,
$R_{23}$ is chosen from:

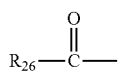

the group
methyl, ethyl or C$_{14}$-C$_{22}$ hydrocarbon-based groups,
a hydrogen atom,
$R_{25}$ is chosen from:

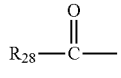

the group
a hydrogen atom,
$R_{24}$, $R_{26}$ and $R_{28}$, which may be identical or different, are chosen from linear or branched, saturated or unsaturated C$_{13}$-C$_{17}$ hydrocarbon-based groups, and more particularly from linear or branched, saturated or unsaturated C$_{13}$-C$_{17}$ alkyl and alkenyl groups.

Advantageously, the hydrocarbon-based radicals are linear.

Among the compounds of formula (VIII), examples that may be mentioned include salts, especially the chloride or methyl sulfate, of diacyloxyethyldimethylammonium, diacyloxyethylhydroxyethylmethylammonium, monoacyl-oxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably methyl or ethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of mono-, di- and triesters with a weight majority of diester salts.

It is also possible to use the ammonium salts containing at least one ester function that are described in U.S. Pat. No. 4,874,554 and U.S. Pat. No. 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

Examples of nonionic surfactants that may be used in the composition used according to the invention and that are different from the surfactants (i) are in particular nonionic surfactants with an HLB of greater than 10, described, for example, in the *Handbook of Surfactants* by M. R. Porter, published by Blackie & Son (Glasgow and London), 1991, pp. 116-178. They are especially chosen from polyethoxylated, polypropoxylated and/or polyglycerolated alcohols, α-diols and ($C_1$-$C_{20}$)alkylphenols, containing at least one fatty chain comprising, for example, from 8 to 18 carbon atoms, the number of ethylene oxide and/or propylene oxide groups possibly ranging especially from 6 to 50, and the number of glycerol groups possibly ranging especially from 2 to 30.

Mention may also be made of copolymers of ethylene oxide and propylene oxide, optionally oxyethylenated fatty acid esters of sorbitan, fatty acid esters of sucrose, polyoxyalkylenated fatty acid esters, optionally oxyalkylenated alkylpolyglycosides, alkylglucoside esters, derivatives of N-alkylglucamine and of N-acylmethylglucamine, aldobionamides and amine oxides.

The nonionic surfactants are more particularly chosen from polyoxyalkylenated and polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include:
  oxyalkylenated ($C_8$-$C_{24}$)alkylphenols;
  saturated or unsaturated, linear or branched, oxyalkylenated $C_8$-$C_{30}$ alcohols;
  saturated or unsaturated, linear or branched, oxyalkylenated $C_8$-$C_{30}$ amides;
  esters of saturated or unsaturated, linear or branched $C_8$-$C_{30}$ acids and of polyethylene glycols;
  polyoxyethylenated esters of saturated or unsaturated, linear or branched $C_8$-$C_{30}$ acids and of sorbitol;
  saturated or unsaturated, oxyethylenated plant oils;
  condensates of ethylene oxide and/or of propylene oxide, inter alia, alone or as mixtures;
  optionally oxyalkylenated alkylpolyglycosides;
  optionally oxypropylenated oxyethylenated silicones.

The surfactants contain a number of moles of ethylene oxide and/or of propylene oxide of between 1 and 100, preferably between 2 and 50 and preferably between 2 and 30. Advantageously, the nonionic surfactants do not comprise any oxypropylene units.

In accordance with one preferred embodiment of the invention, the additional oxyalkylenated nonionic surfactants are chosen from oxyethylenated $C_8$-$C_{30}$ alcohols comprising from 6 to 100 mol of ethylene oxide; polyoxyethylenated esters of linear or branched, saturated or unsaturated $C_8$-$C_{30}$ acids and of sorbitol comprising from 1 to 100 mol of ethylene oxide.

As examples of polyglycerolated nonionic surfactants, monoglycerolated or polyglycerolated $C_8$-$C_{40}$ alcohols are preferably used.

In particular, the polyglycerolated $C_8$-$C_{40}$ alcohols correspond to the following formula:

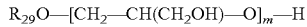

$$R_{29}O\text{---}[CH_2\text{---}CH(CH_2OH)\text{---}O]_m\text{---}H$$

in which $R_{29}$ represents a linear or branched $C_8$-$C_{40}$ and preferably $C_8$-$C_{30}$ alkyl or alkenyl radical, and m represents a number ranging from 4 to 30 and preferably from 4 to 10.

As examples of compounds that are suitable in the context of the invention, mention may be made of lauryl alcohol containing 4 mol of glycerol (INCI name: Polyglyceryl-4 Lauryl Ether), oleyl alcohol containing 4 mol of glycerol (INCI name: Polyglyceryl-4 Oleyl Ether), cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohols may coexist in the form of a mixture.

Preferably, the additional surfactant used in the process of the invention is a nonionic surfactant with an HLB of greater than 10, comprising oxyalkylene units, particularly oxyethylene or oxypropylene units, or a combination thereof, more particularly oxyethylene units.

Non-limiting examples of surfactants with an HLB of greater than or equal to 10 are especially given in the publication entitled *McCutcheon's Emulsifiers & Detergents*, 1998 International Edition, MC Publishing Company, in the chapter entitled HLB Index.

Commercial compounds that may be mentioned include:

| | |
|---|---|
| Cremophor A6 | (BASF) |
| Genapol O-080 | (HOECHST) |
| Genapol T-080 | (HOECHST) |
| Kotilen-O/3 | (KOLB) |
| Lutensol AP 7 | (BASF) |
| Tween 85 | (ICI) |
| Tebecid S8 | (BOHME) |
| Berol 047 | (BEROL NOBEL) |
| Soprophor 860P | (RHONE-POULENC) |
| Dobanol 45-7 | (SHELL) |
| Prox-onic HR-030 | (PROTEX) |
| Ethonic 1214-6,5 | (ETHYL) |
| Prox-onic OA-1/09 | (PROTEX) |
| Cremophor S9 | (BASF) |
| Imbentin AG/128/080 | (KOLB) |
| Serdox NOG 440 | (SERVO) |
| Softanol 70 | (B.P. CHEMICALS) |
| Renex 707 | (ICI) |
| Simulsol 830 NP | (SEPPIC) |
| Brij 76 | (ICI) |
| Tebenal T10 | (BOHME) |
| Volpo S-10 | (CRODA) |
| Eumulgin O10 | (HENKEL) |
| Berol 199 | (BEROL NOBEL) |
| Triton N-87 | (ROHM & HAAS) |
| Polychol 15 | (CRODA) |
| Brij 56 | (ICI) |
| Simulsol 56 | (SEPPIC) |
| Cremophor A11 | (BASF) |
| Eumulgin 286 | (HENKEL) |
| Genapol T-110 | (HOECHST) |
| Sandoxylate FOL12 | (SANDOZ) |
| Bio soft HR 40 | (STEPAN) |
| Berol 046 | (BEROL NOBEL) |
| Eumulgin B1 | (HENKEL) |
| Dobanol 45-11 | (SHELL) |
| Aqualose W20 | (WESTBROCK LANOLIN) |
| Ethylan DP | (HARCROS) |
| Mergital OC12 | (HENKEL) |
| Simulsol 1230 NP | (SEPPIC) |
| Tagat R1 | (GOLDSCHMIDT) |
| Tagat I 2 | (GOLDSCHMIDT) |
| Tebecid RM20 | (BOHME) |
| Imbentin AG/168/150 | (KOLB) |
| Prox-onic LA-1/012 | (PROTEX) |
| Etocas 60 | (CRODA) |
| Radiasurf 7157 | (OLEOFINA) |
| Genapol T-180 | (HOECHST) |
| Montanox 80 | (SEPPIC) |
| Serdox NJAD 20 | (SERVO) |
| Tagat R60 | (GOLDSCHMIDT) |
| Berol 278 | (BEROL NOBEL) |
| Brij 78 | (ICI) |
| Simulsol 98 | (SEPPIC) |
| Montanox 40 | (SEPPIC) |
| Brij 58 | (ICI) |
| Aqualose L75 | (WESTBROCK LANOLIN) |
| Atlas G-1471 | (ICI) |
| Berol 281 | (BEROL NOBEL) |
| Berol 292 | (BEROL NOBEL) |
| Nafolox 20-22 30OE | (CONDEA) |
| Genapol C-200 | (HOECHST) |
| Myrj 51 | (ICI) |
| Simulsol PS 20 | (SEPPIC) |
| Tergitol 15 S 20 | (UNION CARBIDE) |
| Synperonic PE P75 | (ICI) |
| Montanox 20 | (SEPPIC) |
| Myrj 52 | (ICI) |
| Simulsol 3030 NP | (SEPPIC) |
| Imbentin AG/168/400 | (KOLB) |
| Rhodia Surf NP40 | (RHONE-POULENC) |
| Incropol CS-50 | (CRODA) |
| Servirox OEG 90/50 | (SERVO) |
| Prox-onic HR-0200 | (PROTEX) |
| Berol 243 | (BEROL NOBEL) |
| Imbentin N/600 | (KOLB) |
| Antarox CO 980 | (RHONE-POULENC) |
| Antarox CO 987 | (RHONE-POULENC) |
| Berol 08 | (BEROL NOBEL) |
| Brij 700 | (ICI) |
| Prox-onic NP-0100 | (PROTEX) |
| Rs-55-100 | (HEFTI) |
| Imbentin AG/168S/950 | (KOLB) |
| Synperonic PE F87 | (ICI) |
| Alkasurf BA-PE80 | (RHONE-POULENC) |
| Synperonic PE F38 | (ICI) |

In composition (A) and in the ready-to-use composition, the amount of nonionic surfactant(s) in the composition preferably ranges from 0.1% to 30% by weight and better still from 0.2% to 20% by weight relative to the total weight of the composition under consideration, i.e. composition (A) or the ready-to-use composition (mixture (A)+(B)).

Composition (B) may comprise at least one surfactant. If it contains surfactants, their total content may range from 0.1% to 30% by weight and better still from 0.2% to 20% by weight relative to the total weight of composition (B).

(iv)—The Dyes:

The process according to the invention may optionally comprise one or more dyes chosen from a) oxidation dyes and b) direct dyes, or mixtures of a) and b) that will be detailed hereinbelow.

When the process according to the invention is intended for dyeing keratin fibres, composition (A) comprises one or more dyes and preferably a) at least one oxidation dye.

The oxidation dyes are generally chosen from one or more oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloropara-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethyl phenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1 H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Composition (A) according to the invention may optionally comprise one or more couplers advantageously chosen from those conventionally used in the dyeing of keratin fibres.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylamino-benzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxy-ethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are especially chosen from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of composition (A) and of the ready-to-use composition.

The coupler(s), if they are present, each advantageously represent from 0.001% to 10% by weight relative to the total weight of the composition, and preferably from 0.005% to 5% by weight relative to the total weight of composition (A) and of the ready-to-use composition.

Composition (A) according to the invention may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the composition.

According to one preferred embodiment of the invention, the process is a dyeing process and composition (A) and similarly the ready-to-use composition contain at least one dye and preferably at least one oxidation dye as defined previously.

Compositions (A) and (B) and the ready-to-use composition may also contain additional ingredients.

The Additional Solid Fatty Substances:

According to one particular embodiment of the invention, the emulsion (A) may contain at least one fatty alcohol that is solid at room temperature and at atmospheric pressure. The term "fatty alcohol" means a long-chain aliphatic alcohol comprising from 6 to 34 carbon atoms and comprising at least one hydroxyl group OH.

Preferably, the solid fatty alcohols are of structure R—OH with R being a linear alkyl group comprising from 12 to 34 carbon atoms.

The fatty alcohols that are solid at room temperature, which are suitable for use in the invention, are more particularly chosen from:
lauryl alcohol (1-dodecanol);
myristyl alcohol (1-tetradecanol);
cetyl alcohol (1-hexadecanol);
stearyl alcohol (1-octadecanol);
arachidyl alcohol (1-eicosanol);
behenyl alcohol (1-docosanol);
lignoceryl alcohol (1-tetracosanol);
ceryl alcohol (1-hexacosanol);
montanyl alcohol (1-octacosanol);
myricyl alcohol (1-triacontanol); and mixtures thereof.

According to one particular mode of the invention, the solid fatty alcohols of structure R—OH are such that R as defined previously comprises from 12 to 30 and better still 12 to 22 carbon atoms.

Even more particularly, the solid fatty alcohols are chosen from cetyl alcohol, stearyl alcohol, behenyl alcohol and mixtures thereof such as cetylstearyl alcohol or cetearyl alcohol.

Preferably, the content of fatty alcohols that are solid at room temperature and atmospheric pressure in the composition (A) according to the invention is between 0.2% and 20% by weight, preferably from 0.5% to 15% by weight and even more particularly from 1% to 10% by weight relative to the total weight of composition (A).

Composition (B) may also contain one or more solid fatty alcohols. If it contains one or more solid fatty alcohols, the content thereof may range from 0.2% to 20% by weight, preferably from 0.5% to 15% by weight and even more particularly between 1% and 10% by weight relative to the total weight of composition (B).

Preferably, the content of fatty alcohols that are solid at room temperature and atmospheric pressure in the ready-to-use composition according to the invention ranges between 0.2% and 20% by weight, preferably from 0.5% to 15% by weight and even more particularly from 1% to 10% by weight relative to the total weight of composition (A).

Fatty Substances Other than the Oils and the Solid Fatty Alcohols:

Compositions (A) and (B) and the ready-to-use composition may also contain additional fatty substances other than the solid fatty alcohols and the oils mentioned previously.

The additional fatty substance(s) used in the compositions according to the invention may also be fatty substances that are non-oily at room temperature (25° C.) and at atmospheric pressure (760 mmHg, i.e. $1.013 \times 10^5$ Pa).

The term "non-oily" preferably means a solid compound or a compound that has a viscosity of greater than 2 Pa·s at a temperature of 25° C. and at a shear rate of $1\ s^{-1}$.

More particularly, the non-oily fatty substances other than the solid fatty alcohols described previously are chosen from synthetic esters of fatty acids and/or of fatty alcohols, natural waxes, silicone waxes, fatty amides and fatty ethers, which are non-oily and preferably solid.

As regards the non-oily synthetic esters of fatty acids and/or of fatty alcohols, mention may be made especially of solid esters derived from $C_9$-$C_{26}$ fatty acids and from $C_9$-$C_{26}$ fatty alcohols.

Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate and stearyl myristate, and hexyl stearate.

The natural wax(es) are chosen especially from carnauba wax, candelilla wax, esparto wax, paraffin wax, ozokerite, plant waxes such as olive tree wax, rice wax, hydrogenated jojoba wax or absolute flower waxes such as the blackcurrant blossom essential wax sold by the company Bertin (France), and animal waxes such as beeswaxes or modified beeswaxes (cerabellina).

Solid fatty amides that may be mentioned include ceramides. The ceramides or ceramide analogues, such as glycoceramides, that may be used in the compositions according to the invention are known per se and are natural or synthetic molecules that may correspond to the general formula (IX) below:

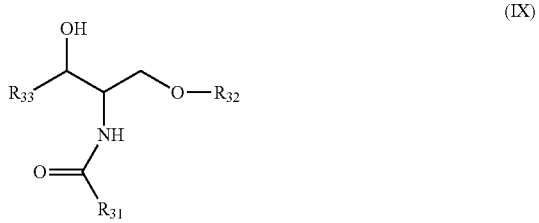

in which formula (IX):
- $R_{31}$ denotes a linear or branched, saturated or unsaturated alkyl radical, derived from $C_{14}$-$C_{30}$ fatty acids, this radical possibly being substituted with a hydroxyl group or a hydroxyl group in the omega position esterified with a saturated or unsaturated $C_{16}$-$C_{30}$ fatty acid;
- $R_{32}$ denotes a hydrogen atom or a radical (glycosyl)n, (galactosyl)m or sulfogalactosyl, in which n is an integer ranging from 1 to 4 and m is an integer ranging from 1 to 8;
- $R_{33}$ denotes a $C_{15}$-$C_{26}$ hydrocarbon-based group which is saturated or unsaturated in the alpha position, it being possible for this group to be substituted with one or more $C_1$-$C_{14}$ alkyl groups;

it being understood that, in the case of these natural ceramides or glycoceramides, $R_3$ may also denote a $C_{15}$-$C_{26}$ α-hydroxyalkyl radical, the hydroxyl group being optionally esterified with a $C_{16}$-$C_{30}$ α-hydroxy acid.

The ceramides that are preferred in the context of the present invention are those described by Downing in Arch. Dermatol., Vol. 123, 1381-1384, 1987, or those described in French patent FR 2 673 179.

The ceramide(s) that are more particularly preferred according to the invention are the compounds for which $R_{31}$ denotes a saturated or unsaturated alkyl derived from $C_{16}$-$C_{22}$ fatty acids; $R_{32}$ denotes a hydrogen atom and $R_{33}$ denotes a saturated linear $C_{15}$ radical.

Such compounds are, for example:
N-linoleyldihydrosphingosine,
N-oleyldihydrosphingosine,
N-palmitoyldihydrosphingosine,
N-stearoyldihydrosphingosine,
N-behenyldihydrosphingosine,
or mixtures of these compounds.

Even more preferentially, use is made of ceramides for which $R_{31}$ denotes a saturated or unsaturated alkyl radical derived from fatty acids; $R_{32}$ denotes a galactosyl or sulfogalactosyl radical; and $R_{33}$ denotes a group —CH=CH—$(CH_2)_{12}$—$CH_3$.

Other waxes or waxy starting materials that may be used according to the invention are especially marine waxes such as those sold by the company Sophim under the reference M82, and waxes of polyethylene or of polyolefins in general, and organopolysiloxane waxes or resins.

The organopolysiloxane resins that may be used in accordance with the invention are crosslinked siloxane systems containing the following units:
$R_2SiO_{2/2}$, $R_3SiO_{1/2}$, $RSiO_{3/2}$ and $SiO_{4/2}$
in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate type resins sold in particular under the names X22-4914, X21-5034 and X21-5037 by the company Shin-Etsu.

The non-oily fatty ethers are chosen from dialkyl ethers and especially dicetyl ether and distearyl ether, alone or as a mixture.

Preferably, the non-oily fatty substance(s) other than the solid fatty alcohols are present in compositions (A) and (B) or in the ready-to-use composition in a content ranging from 0 to 30%.

The Oxidizing Agents:

The oxidizing composition (B) is preferably an aqueous composition. In particular, it comprises more than 5% by weight of water, preferably more than 10% by weight of water and even more advantageously more than 20% by weight of water.

Composition (B) may also comprise one or more organic solvents chosen from those listed previously; these solvents more particularly representing, when they are present, from 1% to 40% by weight and preferably from 5% to 30% by weight relative to the weight of the oxidizing composition.

The oxidizing composition also preferably comprises one or more acidifying agents. Among the acidifying agents, examples that may be mentioned include inorganic or organic acids, for instance hydrochloric acid, orthophosphoric acid, sulfuric acid, carboxylic acids, for instance acetic acid, tartaric acid, citric acid or lactic acid, and sulfonic acids.

Usually, the pH of the oxidizing composition, when it is aqueous, is less than 7.

Composition (B) according to the invention comprises one or more oxidizing agents. More particularly, the oxidizing agent(s) are chosen from hydrogen peroxide, urea peroxide, alkali metal bromates or ferricyanides, peroxygenated salts, for instance alkali metal or alkaline-earth metal persulfates, perborates and percarbonates, and peracids and precursors thereof.

Preferably, the oxidizing agent is not chosen from peroxygenated salts.

Advantageously, the oxidizing agent is hydrogen peroxide.

Preferably, the oxidizing composition (B) comprises hydrogen peroxide as oxidizing agent, in aqueous solution, the concentration of which ranges, more particularly, from 0.1% to 50%, more particularly between 0.5% and 20% and more preferably still between 1% and 15% by weight relative to the weight of the oxidizing composition.

The Other Adjuvants:

Compositions (A) and/or (B) and the ready-to-use composition of the process of the invention may also contain various adjuvants conventionally used in compositions for dyeing or lightening the hair, such as anionic, cationic, nonionic, amphoteric or zwitterionic polymers or mixtures thereof; antioxidants; penetrants; sequestrants; fragrances; dispersants; film-forming agents; preserving agents; opacifiers and thickeners.

The above adjuvants are generally present in an amount, for each of them, of between 0.01% and 20% by weight relative to the weight of the composition.

Compositions (A) and/or (B) and the ready-to-use composition of the process according to the present invention may also comprise one or more mineral thickeners chosen from organophilic clays and fumed silicas, or mixtures thereof.

According to one particular embodiment of the process of the invention, composition (A) does not contain any clay. According to another particular embodiment of the invention, composition (B) does not contain any clay. Preferentially, the process of the invention or the oil-rich direct emulsion obtained from the mixing of compositions (A) and (B) does not use or contain any clay.

Compositions (A) and/or (B) and the ready-to-use composition of the process according to the invention may also comprise one or more organic thickeners.

These thickeners may be chosen from fatty acid amides (coconut monoethanolamide or diethanolamide, oxyethylenated carboxylic acid monoethanolamide alkyl ether), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum), acrylic acid or acrylamidopropane-sulfonic acid crosslinked homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

According to one particular embodiment, the organic thickener is chosen from cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum) and acrylic acid or acrylamidopropane-sulfonic acid crosslinked homopolymers, and preferably from cellulose-based thickeners in particular with hydroxyethylcellulose.

The content of organic thickener(s), if they are present, usually ranges from 0.01% to 20% by weight and preferably from 0.1% to 5% by weight relative to the weight of compositions (A) and (B) and of the ready-to-use composition.

Compositions (A) and/or (B) and the ready-to-use composition according to the invention are media comprising at least water and optionally one or more cosmetically acceptable organic solvents.

Examples of cosmetically acceptable organic solvents that may be mentioned include linear or branched and preferably saturated monoalcohols or diols, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycerol; polyols or polyol ethers, for instance ethylene glycol monomethyl, monoethyl and monobutyl ethers, 2-butoxyethanol, propylene glycol or ethers thereof, for instance propylene glycol, butylene glycol or dipropylene glycol monomethyl ether; and also diethylene glycol alkyl ethers, especially of $C_1$-$C_4$, for instance diethylene glycol monoethyl ether or monobutyl ether, alone or as a mixture.

The solvents, when they are present, generally represent between 1% and 40% by weight relative to the total weight of the dye composition, and preferably between 5% and 30% by weight relative to the total weight of the composition(s) containing them.

Preferably, compositions (A) and/or (B) and the ready-to-use composition of the process of the invention contain water in a content ranging from 10% to 70% and better still from 20% to 55% relative to the total weight of the composition.

Compositions (A) and/or (B) and the ready-to-use composition of the process according to the invention may be in various forms, such as in the form of liquids, creams or gels, or in any other form that is suitable for dyeing keratin fibres, and especially human hair.

Advantageously, compositions (A) and/or (B) and the ready-to-use composition of the process according to the invention are in the form of a gel or cream.

Preferably, the ready-to-use composition resulting from the mixing of compositions (A) and (B) is in the form of a direct emulsion.

The pH of the composition after mixing compositions (A) and (B) of the process according to the invention is advantageously between 3 and 12, preferably between 5 and 11 and preferentially between 7 and 11, limits inclusive.

It may be adjusted to the desired value by means of acidifying or basifying agents usually used in the dyeing of keratin fibres, or alternatively using standard buffer systems.

The alkaline agents are, for example, those described previously.

Examples of acidifying agents that may be mentioned include mineral or organic acids, for instance hydrochloric acid, orthophosphoric acid, carboxylic acids, for instance tartaric acid, citric acid or lactic acid, or sulfonic acids.

Method for Preparing the Direct Emulsion Obtained from the Mixing of (A) and (B):

The ingredients of the abovementioned compositions (A) and (B) and the contents thereof are determined as a function of the characteristics detailed previously for the composition obtained from the final mixture of (A) and (B) according to the invention.

It should be noted that the mixture of compositions (A) and (B) is preferably a direct emulsion.

The composition (A)/composition (B) weight ratio in the mixture preferably ranges from 0.2 to 2, better still from 0.3 to 1 and even better still from 0.5 to 1.

According to one particular embodiment of the invention, the mixture (A) and (B) is prepared by placing composition (A) and composition (B) together in a container and mixing them, preferentially vigorously, for a few seconds to a few minutes, before application to the keratin fibres. This mixing may be performed using a multi-compartment device or kit as defined below, one of the compartments of which is devoted to the mixing of compositions (A) and (B) and may be shaken in a closed vessel entirely safely, until a homogeneous emulsion is obtained.

The ready-to-use composition obtained from the mixing of compositions (A) and (B) is such that, preferably, the content of fatty substance ranges from 25% to 80% by weight, preferably from 25% to 65% by weight and better still from 30% to 55% by weight relative to the total weight of the mixture of compositions (A) and (B).

A subject of the invention is also a composition (A) in direct emulsion form comprising at least 30% by weight of oil(s) relative to the weight of composition (A), and also comprising:
i) at least one nonionic surfactant that is solid at room temperature and at atmospheric pressure, with an HLB ranging from 1.5 to 10;
ii) at least one basifying agent;
iii) optionally at least one additional surfactant other than the solid nonionic surfactants i), which is preferably nonionic with an HLB of greater than 10;
iv) optionally at least one dye.

Preferably, the composition does not comprise any chemical oxidizing agent.

Another subject of the invention is represented by a ready-to-use composition for dyeing or lightening human keratin fibres, which may be obtained by extemporaneous mixing, at the time of use, of a composition (A) with a composition (B); the resulting mixture comprising at least 25% by weight of fatty substance relative to the total weight of the mixture of compositions (A) and (B); compositions (A) and (B) being defined previously.

In other words, this composition comprises at least 25% by weight of a mixture of fatty substances comprising at least one oil;
i) at least one nonionic surfactant that is solid at room temperature and at atmospheric pressure, with an HLB ranging from 1.5 to 10;
ii) at least one basifying agent;
iii) optionally at least one additional surfactant other than the solid nonionic surfactants (i);
iv) optionally at least one dye; and
at least one chemical oxidizing agent.

II—The Multi-Compartment Devices:

The invention also relates to a device containing two or more compartments, comprising:
in a first compartment, a composition (A) as defined previously; and
in another compartment, a composition (B) as defined previously.

The example that follows serves to illustrate the invention without, however, being limiting in nature.

EXAMPLE

Composition (A) in direct emulsion form below is prepared (the amounts are expressed on a weight basis, i.e. as g % of starting material in unmodified form):

| Composition (A) | % by weight |
|---|---|
| (50/50 $C_8/C_{10}$)Alkyl polyglucoside [Oramix CG 110 containing 60% AM] | 2 |
| Steareth-2 | 2.25 |
| Steareth-20 | 7.75 |
| Liquid petroleum jelly | 60 |
| Monoethanolamine | 4.09 |
| Sodium metabisulfite | 0.45 |
| EDTA | 0.2 |
| 1-β-Hydroxyethyloxy-2,4-diaminobenzene dihydrochloride | 0.017 |
| 1,3-Dihydroxybenzene | 0.51 |
| 1-Methyl-2,5-diaminobenzene | 0.53 |
| 1-Hydroxy-3-aminobenzene | 0.077 |
| Fragrance | 0.6 |
| Ascorbic acid | 0.25 |
| Water | qs 100 |

* Steareth-2: polyethylene glycol stearyl ether of the following formula $CH_3(CH_2)_{16}CH_2(OCH_2CH_2)_2OH$.
** Steareth-20: polyethylene glycol stearyl ether of the following formula $CH_3(CH_2)_{16}CH_2(OCH_2CH_2)_{20}OH$.

Composition (B) below is prepared (the amounts are expressed on a weight basis, i.e. as g % of starting material):

| Composition (B) | % by weight |
|---|---|
| Poly[(dimethyliminio)-1,3-propanediyl(dimethyliminio)-1,6-hexanediyl dichloride] as an aqueous 60% solution (Mexomer PO from Chimex) | 0.25 |
| Diethylenetriaminepentaacetic acid, pentasodium salt as an aqueous 40% solution | 0.15 |
| Rapeseed acid amide containing 4 OE (Amidet N from Kao) | 1.3 |
| Hydrogen peroxide | 6 |
| Glycerol | 0.5 |
| Cetylstearyl alcohol (Nafol 1618S from Sasol) | 6 |
| Stearyl alcohol containing 2 OE (Brij S20-SO from Croda) | 5 |
| Liquid petroleum jelly | 20 |
| Hydrogen peroxide stabilizer | qs |
| Tetrasodium pyrophosphate decahydrate | 0.03 |
| Polydimethyldiallylammonium chloride at 40% in water (Merquat 100 from Nalco) | 0.5 |
| Phosphoric acid | qs pH |
| Water | qs 100 |

Compositions (A) and (B) are mixed together in a 1/1 ratio. The mixing is performed easily.

Mode of Application

The resulting mixture is then applied to locks of natural dark chestnut-brown hair (tone depth TD=3), at a rate of 10 g of mixture per 1 g of hair. The application is easy and the product remains localized at the site of application.

The mixture is left on at room temperature (25° C.) for 30 minutes. There is no unpleasant odour during the application.

The hair is then rinsed, washed with a standard shampoo and dried.

Natural light chestnut-brown locks (TD=5) with good colour intensity are obtained.

The invention claimed is:

1. A process for dyeing or lightening keratin fibers, comprising:
(i) extemporaneously mixing at the time of use
(a) a composition (A) in direct emulsion form comprising:
at least one nonionic surfactant having an HLB ranging from about 1.5 to about 10, which is solid at room temperature and at atmospheric pressure;
at least one basifying agent;
optionally at least one additional surfactant other than the at least one nonionic surfactant;
optionally at least one dye; and
at least about 30% by weight of at least one oil, and
(b) a composition (B) comprising at least one chemical oxidizing agent; and
(ii) applying the mixture to the keratin fibers;
wherein the mixture comprises at least about 25% by weight of fatty substances relative to the total weight of the mixture (A)+(B).

2. The process according to claim 1, wherein the at least one oil is present in an amount of at least about 50% by weight, relative to the total weight of composition (A).

3. The process according to claim 1, wherein the at least one nonionic surfactant is chosen from oxyalkylenated and glycerolated nonionic surfactants.

4. The process according to claim 1, wherein the at least one nonionic surfactant is chosen from:
oxyalkylenated ($C_8$-$C_{24}$)alkylphenols;
saturated and unsaturated, linear and branched, oxyalkylenated $C_8$-$C_{30}$ alcohols;
saturated and unsaturated, linear and branched, optionally oxyalkylenated $C_8$-$C_{30}$ amides;
esters of saturated and unsaturated, linear and branched $C_8$-$C_{30}$ acids and of polyethylene glycols;

optionally polyoxyethylenated esters of saturated and unsaturated, linear and branched $C_8$-$C_{30}$ acids and of sorbitol;

polyglycerolated esters of saturated and unsaturated, linear and branched $C_8$-$C_{30}$ acids;

saturated and unsaturated oxyethylenated plant oils;

$C_8$-$C_{30}$ alkyl glucosides;

condensates of ethylene oxide, condensates of propylene oxide, and condensates of mixtures of ethylene oxide and of propylene oxide; and oxyethylenated and oxypropylenated silicones.

5. The process according to claim 1, wherein the at least one nonionic surfactant is chosen from mono- and polyoxyalkylenated nonionic surfactants.

6. The process according to claim 5, wherein the mono- and polyoxyalkylenated nonionic surfactants comprise oxyalkylene units are chosen from oxyethylene and oxypropylene units.

7. The process according to claim 1, wherein the at least one nonionic surfactant is chosen from solid nonionic surfactants having an HLB ranging from about 2.5 to about 8.

8. The process according to claim 1, wherein the amount of the at least one nonionic surfactant is present in an amount ranging from about 0.1% to about 30% by weight, relative to the total weight of the composition (A).

9. The process according claim 1, wherein the at least one oil is chosen from $C_6$-$C_{16}$ lower alkanes; non-silicone oils of animal origin; glycerides of plant and synthetic origin; linear and branched hydrocarbons of mineral and synthetic origin comprising more than 16 carbon atoms; fluoro oils; liquid fatty alcohols; liquid fatty esters; non-salified liquid fatty acids; silicone oils; and mixtures thereof.

10. The process according to claim 1, wherein the at least one oil is chosen from isododecane and mineral oils.

11. The process according to claim 1, wherein the at least one basifying agent is chosen from aqueous ammonia, alkali metal carbonates and bicarbonates, sodium hydroxide and potassium hydroxide.

12. The process according to claim 1, wherein the at least one basifying agent is chosen from organic amines.

13. The process according to claim 1, wherein the at least one additional surfactant other than the at least one nonionic surfactant is chosen from nonionic surfactants having an HLB of greater than about 10.

14. The process according to claim 1, wherein the at least one dye is chosen from oxidation dyes, direct dyes, and mixtures thereof.

15. The process according to claim 1, wherein the at least one dye is an oxidation dye chosen from oxidation bases and the addition salts thereof, optionally combined with at least one coupler chosen from meta-phenylenediamines, meta-aminophenols, meta-diphenols, naphthalene-based couplers, heterocyclic couplers, and the addition salts thereof.

16. The process according to claim 1, wherein composition (A) does not contain an oxidation base, coupler, or direct dye.

17. The process according to claim 1, wherein the at least one oxidizing agent is chosen from hydrogen peroxide, urea peroxide, alkali metal bromates and ferricyanides, peroxygenated salts, peracids, and precursors thereof.

18. A device comprising:
(i) in a first compartment, a composition (A) comprising:
  at least one nonionic surfactant having an HLB ranging from about 1.5 to about 10, which is solid at room temperature and at atmospheric pressure;
  at least one basifying agent;
  optionally at least one additional surfactant other than the at least one nonionic surfactant;
  optionally at least one dye; and
  at least about 30% by weight of at least one oil; and
(ii) in a second compartment, a composition (B) comprising at least one chemical oxidizing agent.

* * * * *